(12) United States Patent
Lüll et al.

(10) Patent No.: US 8,255,239 B2
(45) Date of Patent: Aug. 28, 2012

(54) ACCESS CONTROLLER AND METHOD FOR CONTROLLING ACCESS TO MEDICAL DATA

(75) Inventors: Catrin Lüll, Grossenseebach (DE); John Sanchez, Nürnberg (DE); Sandra Sodilo, Mockmühl (DE)

(73) Assignee: Siemens Aktiengesellschaft, Munich (DE)

( * ) Notice: Subject to any disclaimer, the term of this patent is extended or adjusted under 35 U.S.C. 154(b) by 1250 days.

(21) Appl. No.: 11/348,682

(22) Filed: Feb. 7, 2006

(65) Prior Publication Data

US 2007/0233639 A1 Oct. 4, 2007

(30) Foreign Application Priority Data

Feb. 7, 2005 (DE) .......................... 10 2005 005 601

(51) Int. Cl.
*G06Q 10/00* (2012.01)
(52) U.S. Cl. ................. 705/3; 705/2; 600/300; 600/301
(58) Field of Classification Search .................. 705/2, 3, 705/4
See application file for complete search history.

(56) References Cited

U.S. PATENT DOCUMENTS

| 6,915,265 B1 * | 7/2005 | Johnson ............................ 705/2 |
| 7,395,214 B2 * | 7/2008 | Shillingburg ...................... 705/2 |
| 7,424,679 B1 * | 9/2008 | Lamer et al. .................. 715/737 |
| 7,461,079 B2 * | 12/2008 | Walker et al. ................. 707/102 |
| 2003/0156745 A1 | 8/2003 | Saito et al. |
| 2003/0177038 A1 | 9/2003 | Rao |
| 2004/0128323 A1 | 7/2004 | Walker et al. |
| 2006/0013457 A1 | 1/2006 | Ritter |

FOREIGN PATENT DOCUMENTS

| DE | 103 06 796 A1 | 9/2004 |
| WO | WO 03/046810 | 6/2003 |

OTHER PUBLICATIONS

Digital Imaging and Communications in Medicine (DICOM), DICOM Standards Committee (2000).

\* cited by examiner

*Primary Examiner* — Vivek Koppikar
*Assistant Examiner* — Edward Winston, III
(74) *Attorney, Agent, or Firm* — Schiff Hardin LLP

(57) ABSTRACT

In an access controller and method for controlling access to medical data, the medical data being provided as at least one first file and a second file independent of the first file with findings regarding patients that are generated by medical personnel being stored in the first file and measurement results of patients that were acquired by means of a medical-technical apparatus being stored in the second file, with at least one subset of the measurement results stored in the second file forming the basis of at least a subset of the findings stored in the first file, the access controller is configured to detect the measurement results forming the basis of a stored finding. Links to the measurement results forming the basis of a respective finding are stored at the findings in the first file and the access controller is configured to automatically detect measurement results stored in the second file and form the basis of a finding, the automatic detection ensuing using the link stored at the respective finding in the first file.

13 Claims, 5 Drawing Sheets

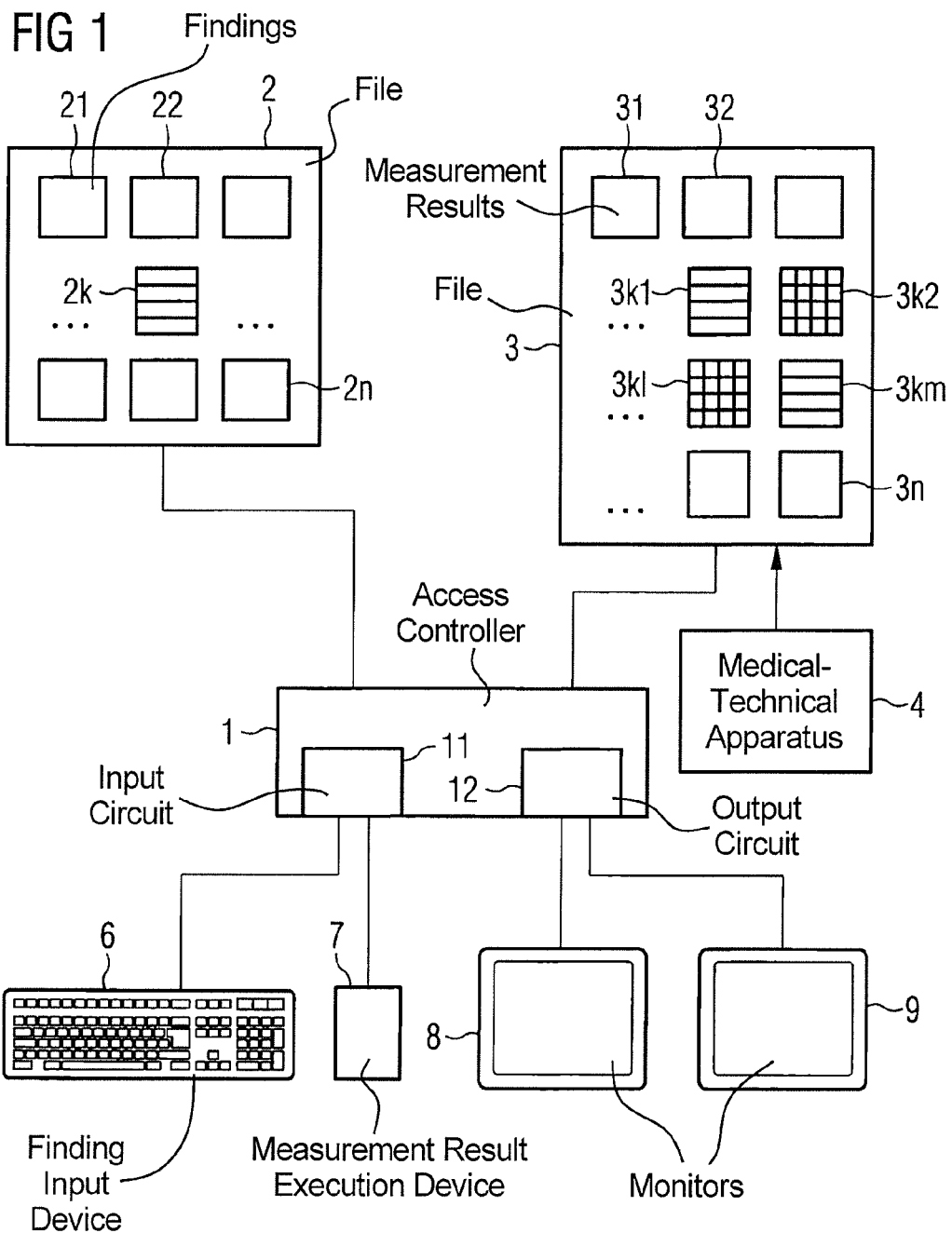

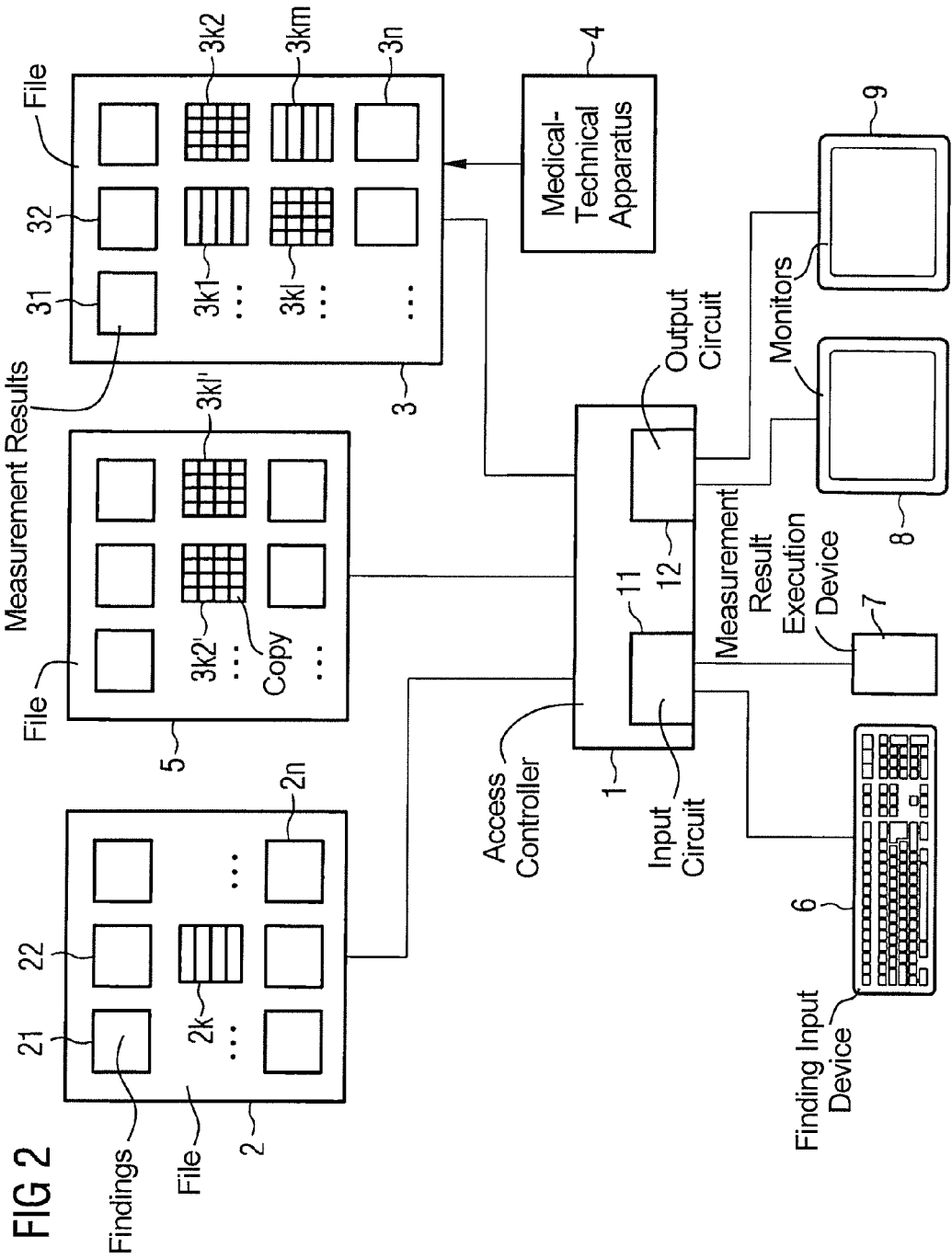

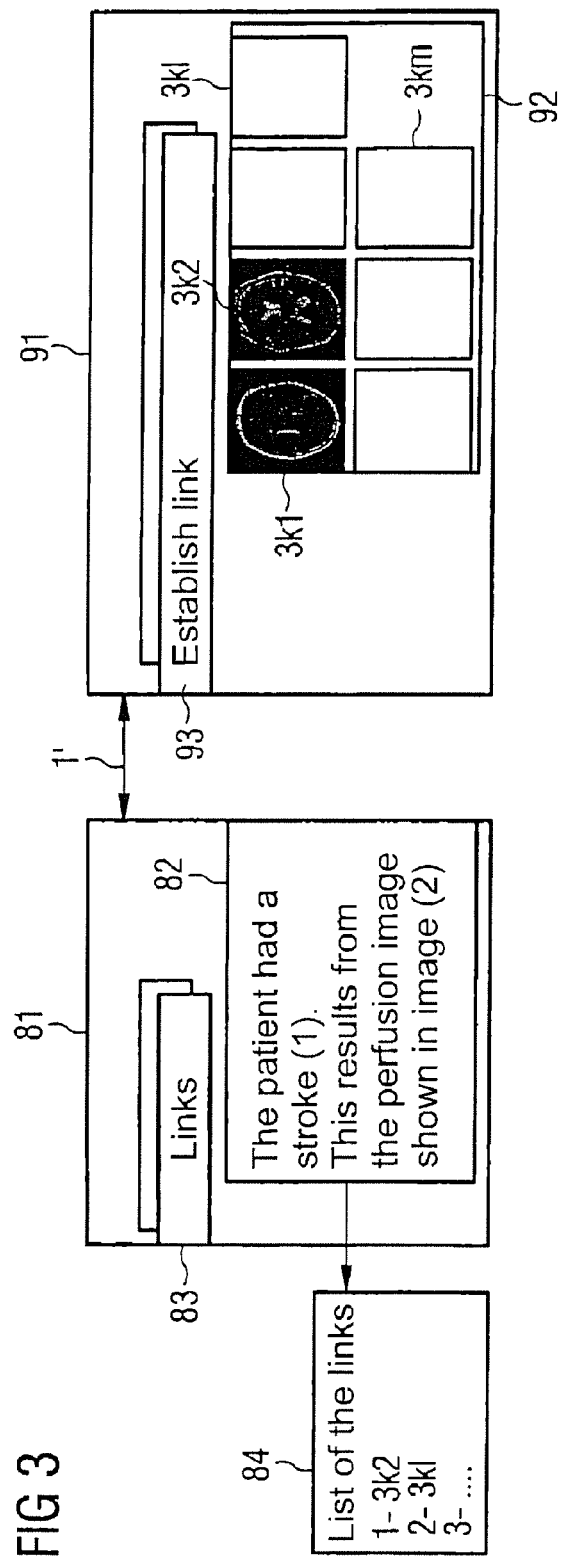

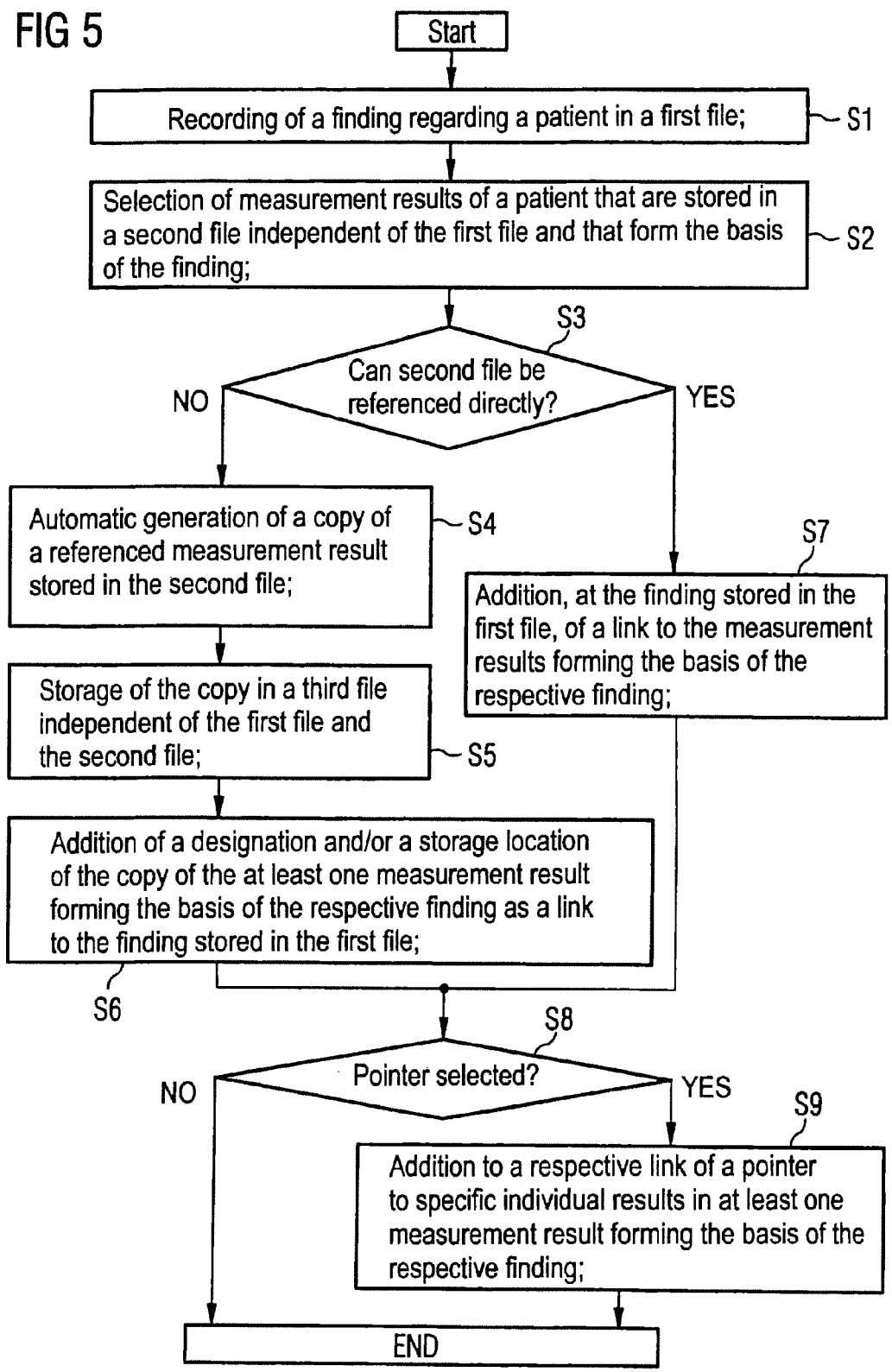

ACCESS CONTROLLER AND METHOD FOR CONTROLLING ACCESS TO MEDICAL DATA

BACKGROUND OF THE INVENTION

1. Field of the Invention

The present invention concerns an access controller for controlling access to medical data as well as for controlling access to medical data.

2. Description of the Prior Art

In the field of medical technology, frequently a first doctor examines a patient and generates a finding based on the examinations, followed by a treatment of the patient by a second doctor using the finding made by the first doctor. The first doctor typically bases the generation of the finding on diverse measurement results of the patient such as, for example, x-ray images or CT images.

For the first assessing doctor, it is frequently necessary to review a number of measurement results of the patient to produce a finding, but often only a small subset of the available measurement results of the patient are relevant for the actual finding.

The finding generated in this manner typically is written in a patient file by the first doctor for reproduction at the treating second doctor. The measurement results (for example the x-ray images of the patient) normally remain with the assessing doctor, and only the patient file with the finding is forwarded to the doctor conducting the further treatment.

In modern hospitals it is known to store the patient file of the patient in digital form in a first file and to store the measurement results (such as subtraction angiography x-ray images of the patient) in a second file independent of the first file, in order to increase the availability of both the patient file and the measurement results.

In general, the findings of the patient that are stored in the first file are stored wholly independent of the measurement results of the patient that are stored in the second file.

The digital patient files with the findings are frequently stored in an RIS databank and the measurement results used to generate the findings are frequently stored in a PACS databank. Although the RIS databank can be integrated into the PACS databank, a linking of the entries in the RIS databank to entries in the PACS databank conventionally occurs only in a limited manner. In known systems it is thus possible to open the measurement results in the PACS databank that are associated with the patient entry by double-clicking on a patient entry in the RIS databank. A link between the RIS and the PACS databank, however, exists only across the same patient entries and not with regard to individual findings.

Various requirements are placed on the generation of a finding in a medical patient file. The perception and experience of the finding doctor should enter into the finding. Normally the findings are therefore structured in two parts. The state of the patient established from the measurement results is discussed briefly in a first part and a short conclusion is drawn from this in a second part.

The classical finding written in a patient file thus corresponds to the inductive procedure in which facts are weighed and a conclusion is drawn therefrom.

The previously described conventional design of a finding has various disadvantages. It is necessary for the doctor performing further treatment to read the entire finding until that doctor comes to the end of the result. This is particularly disadvantageous given the use of digital patient files since the doctor performing further treatment in this case must frequently page or scroll through various pages.

A different design of findings is therefore to be chosen given the use of digital patient files:

The most important assessments and conclusions should initially be sorted according to their importance. A comparison with the measured measurement results should subsequently be possible. This comparison is very important in order to preclude malpractice, since without such a comparison it is not possible for a doctor performing further treatment to be able to establish incorrect findings of the assessing doctor. Furthermore, via such a comparison it is possible to render the finding more concretely and to make it more comprehensible at a later point in time. The omission of a comparison of the finding with the measured measurement results can make a doctor performing further treatment liable for damages.

In order to enable such a comparison in findings written down in digital patient files, it is known for the finding doctor to manually characterize the measurement results used for the finding with an identification character. This identification character is stored in the second file as a data attribute together with the measurement result and allows the second file to be searched for according to the identification character.

This procedure has the disadvantage that a doctor performing further treatment must not only study the patient file of the patient that is written in the first file in order to arrive at knowledge of a finding, but also must set up a filter function using this finding for searching through the second file which contains the measurement results.

Such a filter function typically includes a patient identification as well as the identification character.

It should be emphasized that no indication of the identification character associated with the measurement result stored in the second file is contained in the finding stored in the first file. Rather, in the search for measurement results forming the basis of a finding, the doctor performing further treatment must search for the filter function using a library of suitable identification characters. As a result, the addition of identification characters to the measurement results stored in the second file does not result in an effective relation to the findings stored in the first file.

It is thus always necessary to search through the entire second file for measurement results with the identification character, which causes an increased network traffic and an increased computer capacity requirement. Furthermore, errors frequently occur in the arrangement of the filter function that lead to the situation of measurement results that play no role whatsoever for the respective finding being provided to the doctor performing further treatment. The acceptance of the previously known systems is low as a consequence of this.

A further disadvantage of the marking of the measurement results with identification characters is that a file attribute must be added to the measurement results. This requires a clean definition of the identification characters in order to enable a later filtering with high reliability, and is therefore very inflexible.

SUMMARY OF THE INVENTION

It is an object of the present invention to provide an access controller and a method for controlling the access to medical data, that enable access in a particularly simple and reliable manner to measurement results stored in the second file and forming the basis of a finding stored in a first file, and that thereby avoid the disadvantages of the above-described prior art.

This object is achieved in accordance with the invention by an access controller for controlling the access to medical data, wherein the medical data are provided as at least one first file and a second file independent of the first file; and findings regarding the patient that are generated by medical personnel are stored in the first file and measurement results of patients that are acquired by means of a medical technical apparatus are stored in the second file. At least one subset of the measurement results stored in the second file forms the basis of at least one subset of the findings stored in the first file; and the access controller detects the measurement results forming the basis of a stored finding. According to the invention, links to measurement results forming the basis of the respective findings are stored in the first file at the respective findings, and the access controller automatically detects the measurement results stored in the second file that form the basis of a finding, the detection ensuing using the link stored at the respective finding in the first file.

Since links to the measurement results forming the basis of the respective findings are inventively stored in the first file at the respective findings, a real link is produced between the findings stored in the first file and measurement results stored in the second file therefore relevant for the generation of the respective finding. This has various advantages.

The direct reference of the measurement result drawn upon for the generation of a respective finding initially leads to a significant time savings. For example, in a typical hospital it is not unusual for 100,000 x-ray images per year to be checked by doctors performing further treatment together with reading the findings of respective patients. Under the assumption that the inventive use of links (stored together with the findings in the first file) to the respective measurement results achieves merely a 90-second time saving, relative to the solutions known from the prior art, in the access to a measurement result forming the basis of the respective finding, based on an hourly rate of 100 Euro for a doctor, this leads to a savings of over 250,000 Euro per year. Given a less conservative calculation in which the time savings for the access to a measurement result forming the basis of the respective finding amounts to 3 minutes per access, by means of the inventive access controller, this time savings leads to a monetary savings of a half-million Euro per year.

Furthermore, the inventive links (which links are stored in the first file at the respective findings) to the measurement results located in the second file (which measurement results were relevant in the generation of a respective finding) ensure that only actually-relevant measurement results are drawn upon by a doctor performing further treatment given a reading and checking of the finding. The risk of an arbitrary number of unsuitable measurement results being inadvertently output to the doctor performing further treatment due to the use of an incorrect filter thus does not exist, which is different than given the use of identification characters and filter functions known from the prior art. The network traffic to the file in which the measurement results are stored thus is significantly reduced. The required computer capacity is also reduced since no complicated filter functions must be executed. A further time savings is additionally achieved by the avoidance of the output of inapplicable measurement results, since a doctor performing further treatment must check a smaller number of measurement results on average.

Furthermore, the complicated use of identification characters (and therewith file attributes) for the measurement results stored in the second file is avoided by the inventive storage (at findings stored in the first file) of links to measurement results stored in the second file. This simplifies the complexity and clarity of the system. Furthermore, less storage space is necessary for storage of the measurement results in the second file.

The link advantageously specifies a designation and/or a storage location of the at least one measurement result forming the basis of the respective finding.

Due to the design of the link as a designation or specification of a storage location of the at least measurement result forming the basis of the respective finding, the establishment of a reference between the findings of the patient that are stored in the first file and the measurement results of the patient that are stored in the second file is possible in a particularly simple, clear and intuitive manner.

In a preferred embodiment, the access controller is fashioned in order to allow an addition of a link to a finding stored in the first file, and upon addition of a link to a finding the access controller automatically generates a copy of the referenced measurement result and stores the copy in a third file independent of the first file and second file, the link specifying a designation and/or a storage location of the copy of the at least one measurement result forming the basis of the respective finding.

By means of the inventive access controller, by the use of the copy it is possible to reference measurement results that are stored in a second file, the file structure/design of which measurement results does not enable a direct referencing. Since the copies are generated for relevant measurement results, the additional storage space for the copies of the measurement results can be kept low.

The link preferably additionally includes a pointer to specific individual results in an at least one measurement result forming the basis of the respective finding.

The measurement results forming the basis of a finding frequently exhibit a certain complexity. For example, in the case of a CT scan comprising 100 images, or a cardiogram over several minutes, frequently only some images or a few seconds are relevant. Because the link additionally includes a pointer to specific individual results in at least one measurement result forming the basis of the respective finding, the attention of a doctor performing further treatment can be specifically directed to the relevant parts of a respective measurement result and further time thus can be saved. Moreover, an even better clarification of which the measurement results was used to generate a particular finding.

Furthermore, it is advantageous when the access controller also has a finding input device and a measurement result selection device, whereby the finding input device allowing the location of findings regarding patients and the measurement result selection device allowing the selection of measurement results of the patient that are stored in the second file and form the basis of the finding. The access controller is fashioned to automatically generate a link to these measurement results based on the selected measurement results and to store this link at the finding in the first file.

By means of the inventive access controller it is thus not only possible, in a simple, reliable and secure manner, to detect by means of the links the measurement results stored in a second file and forming the basis of a finding of the first file, but also it is possible to store such links at a respective finding in the first file.

In a preferred embodiment, the measurement results are images of the patient acquired by means of one or more imaging medical-technical apparatuses.

Given such imaging apparatuses, a number of measurement results (and thus a number of images to be assessed) normally accumulate, but experience shows that only a small part of the images is relevant for the generation of a finding.

In a further embodiment of the present invention, the first file and/or the second file is a databank file and the findings or measurement results are entries in the respective databank file.

In another embodiment, the first file and/or the second file is a folder file and the findings or measurement results are subordinate files in the respective folder file.

The storage facilities typically used for the first and second file can consequently be retained.

The first file and/or the second file preferably are stored in physically different data memories.

The aforementioned object also is achieved by a method for controlling access to medical data, wherein the medical data are provided as at least one first file and a second file independent from the file; and findings regarding patients that are generated by medical personnel are stored in the first file; and measurement results of patients that were acquired by means of a medical-technical apparatus are stored in the second file; and wherein at least one subset of the measurement results stored in the second file form the basis of at least a subset of the findings stored in the first file, the method including the following steps of adding a link to the measurement results forming the basis of a respective finding at the findings stored in the first file, and automatically detecting measurement results stored in the second file and forming the basis of a finding, using the link stored at the respective finding in the first file.

It is advantageous for the step of the addition of a link at a finding also to include the steps of the automatic generation of a copy of the referenced measurement result and storage of the copy, with a designation and/or a storage location of the copy of the at least one measurement result forming the basis of the respective finding being added at the respective finding as a link.

The step of the adding a link at a finding preferably includes the step of adding of a pointer to specific individual results in at least one measurement result forming the basis of the respective finding.

According to a preferred embodiment, the method also includes the following steps of recording findings regarding patients, selecting measurement results of the patient that are stored in the second file and form the basis of the finding, automatically generating a link to these measurement results based on the selected measurement results, and automatically storing the link at the finding in the first file.

DESCRIPTION OF THE DRAWINGS

FIG. 1 schematically illustrates the design of the inventive access controller according to a first embodiment.

FIG. 2 schematically illustrates the design of the inventive access controller according to a second embodiment.

FIG. 3 schematically illustrates the display of a first display device for display of the first file and the display of a second display device for display of the second file.

FIG. 5 is a flowchart of the inventive method for controlling the access to medical data.

DESCRIPTION OF THE PREFERRED EMBODIMENTS

Figure 4A:
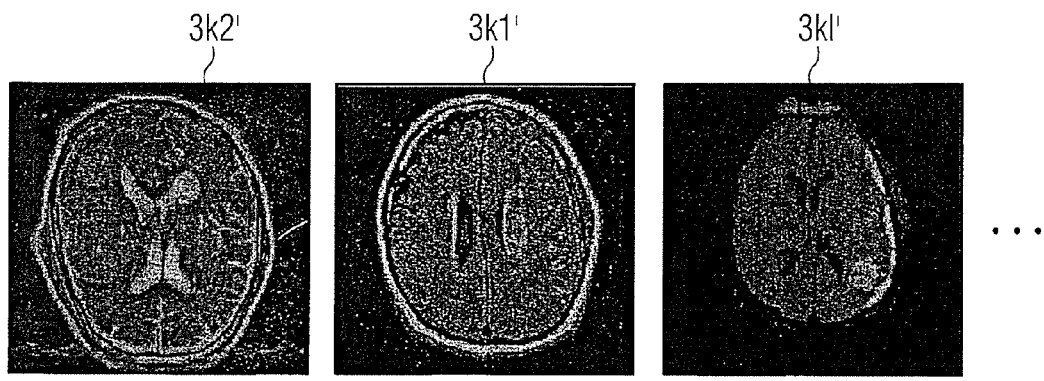
FIG. 4A is a first example of measurement results stored in the second file.

FIG. 1 shows the design of a system for administration of medical data in which the inventive access controller 1 is used to control the access to medical data.

A first file 2 which contains findings $21, 22, \ldots, 2k, \ldots, 2n$ regarding patients that are generated by medical personnel is stored on the hard disk of a first server in the system shown in FIG. 1. In the present example, the first file 2 is an RIS databank file, such that the findings $21, 22, \ldots, 2k, \ldots, 2n$ are entries in the RIS databank file.

Alternatively, the first file 2 can be a folder file and the findings $21, 22, \ldots, 2k, \ldots, 2n$ can be subordinate files in the folder file.

Furthermore, the system shown in FIG. 1 has a second file 3 that is stored on a second server independent of the first server and contains measurement results $31, 32, \ldots, 3k1, 3k2, \ldots, 3kl, \ldots, 3km, \ldots, 3kn$ of patients that were acquired by means of a medical-technical apparatus 4.

In the exemplary embodiment, the measurement results $31, 32, \ldots, 3k1, 3k2, \ldots, 3kl, \ldots, 3km, \ldots, 3kn$ stored in the second file are images of patients that are acquired by means of an imaging medical-technical apparatus 4, for example an x-ray apparatus, a computed tomography apparatus or a magnetic resonance tomography apparatus. These images form the entries of a PACS databank file which forms the second file 3.

Alternatively, the second file 3 can be a folder file and the measurement results $31, 32, \ldots, 3k1, 3k2, \ldots, 3kl, \ldots, 3km, \ldots, 3kn$ can be subordinate files in the folder file.

Since the first file 2 and the second file 3 are stored at different servers and thus at physically different data memories, the first file and the second files 2, 3 are independent of one another.

Alternatively, the first file and second files 2, 3 can be stored on a common server.

The second server 3 is connected with the imaging medical-technical apparatus 4, such that the images acquired by means of the imaging medical-technical apparatus 4 can be centrally stored in the second file 3. It is thus apparent that the second server can be connected not only with a single imaging medical-technical apparatus 4, but rather advantageously is connected with a number of such apparatuses and is fashioned to store in the second file 3 all measurement results of the apparatuses connected with it.

Alternatively, the apparatuses can be non-imaging medical-technical apparatuses that are suitable to acquire measurement results of a patient in the form of individual results, studies or series of studies.

The inventive access controller 1 is connected with the first server containing the first file 2 and the second server containing the second file 3.

In FIG. 1, the finding $2k$ in the first file 2 and the measurement results $3k1, 3k2, \ldots, 3kl, \ldots, 3km$ stored in the second file 3 concern a specific patient k. However, only the images $3k2, \ldots, 3kl$ stored in the second file 3 were drawn upon for the generation of the finding $2k$ stored in the first file 2. A subset $3k2, \ldots, 3kl$ of the measurement results $31, 32, \ldots, 3k1, 3k2, \ldots, 3kl, \ldots, 3km, \ldots, 3kn$ stored in the second file 3 consequently form the basis of the finding $2k$ stored in the first file 2.

Although this is shown in FIG. 1 with regard to only a single finding $2k$ for a single patient k, it is clear that both multiple findings regarding a single patient and various findings regarding various patients that are at least partially based on measurement results stored in the second file 3 can be stored in the first file 2.

According to the invention, electronic links to the measurement results $3k2, \ldots, 3kl$, which form the basis of the respective findings and that are stored in the second file 3 at the second server, are stored in the findings $21, 22, 2k, 2n$ stored in the first file 2 on the first server. In the present example, the electronic link is formed by a designation and a specification of the storage location of the at least one measurement result forming the basis of the respective finding.

For this purpose, in the exemplary embodiment an unambiguous individual or study or series identification is allocated to every individual result (for example image) stored in the second file 3 as well as to every study stored in the second file 3 and every series of studies stored in the second file 3. In the generation of the link to measurement results $3k2, \ldots, 3k1$ forming the basis of a respective finding $2k$, it is sufficient to specify the unambiguous image identification. Naturally, further information such as patient identification, series or study identification such as the name of the second server can also additionally be contained in a respective link.

The inventive access controller 1 connected with the first server and the second server is fashioned to automatically detect the measurement results $3k2, \ldots, 3kl$ stored in the second file 3 and forming the basis of the respective finding $2k$ using a link contained in a finding $2k$ of a patient that is stored in the first file 2.

In FIG. 1, the access controller 1 is also connected with a finding input device 6 and a measurement result execution device 7 via an input circuit 11 as well as with two monitors 8 and 9 via an output circuit 12.

The finding input device 6 is formed by a keyboard and the measurement result execution device 7 is formed by a mouse.

In the exemplary embodiment, the first monitor 8 serves to display a finding $2k$ of a patient k that is stored in the first file 2, in contrast to which the second monitor 9 serves to display the corresponding measurement results $3k1, 3k2, \ldots, 3kl, \ldots, 3km$ regarding the patient k that are stored in the second file 3.

An existing finding stored in the second file 2 can be changed or a new finding regarding a patient can be entered by medical personnel and stored in the first file 2 via the keyboard 6. At the same time, the mouse 7 allows the selection of the respective measurement results $3k2, \ldots, 3kl$ output on the second monitor 9 and stored in the second file, which measurement results $3k2, \ldots, 3kl$ were drawn upon by the medical personnel generating the finding $2k$ for the generation of the finding.

Based on this selection, the access controller 1 is configured to automatically store a link to these measurement results in the form of a specification of the individual image identification at the respective finding $2k$ in the first file 2.

A pointer 10 can be stored that indicates specific individual results in at least one measurement result forming the basis of the respective finding $2k$ in order to simplify the overview given complex measurement results.

A second preferred embodiment of the system for controlling the access to medical data is shown in FIG. 2.

This embodiment differs from the first embodiment described in the preceding in that the second file 3, due to its specific format or design, is not suitable to allow an unambiguous referencing of measurement results $31, 32, \ldots, 3k1, 3k2, \ldots, 3kl, \ldots, 3km, \ldots, 3n$ externally stored in the second file 3.

Furthermore, the example shown in FIG. 2 differs from the example shown in FIG. 1 in that the first file 2 and the second file 3 are different files independent of one another that, however, are stored at a single server.

In order to nevertheless enable in the findings $21, 22, \ldots, 2k, \ldots, 2n$ stored in the first file 2 the generation of an unambiguous electronic link to the measurement results $31, 32, \ldots, 3k1, 3k2, \ldots, 3kl, \ldots, 3km, \ldots, 3kn$ stored in the second file 3, the access controller 1 is furthermore configured to automatically store a copy $3k2', \ldots, 3kl'$ of the referenced measurement result $3k2, \ldots, 3kl$ in a third file 5 independent of the first and second file 2, 3 upon addition at a finding of a link to a measurement result.

In this case, the electronic link stored at a respective finding $2k$ in the first file advantageously, automatically specifies a designation and/or a storage location of the copy $3k2', \ldots, 3kl'$ (stored in the third file 5) of the at least one measurement result $3k2, \ldots, 3kl$ stored in the second file 3 and forming the basis of the respective finding $2k$.

The addition by a user of a link to a measurement result at a finding advantageously ensues via selection of the respective measurement result by means of the keyboard 6 or the mouse 7.

According to this embodiment, referencing is thus also possible to measurement results that are stored in a file which, due to its specific design, makes a direct referencing difficult or impossible.

Examples of monitor displays of the respective monitors 8 and 9 connected with the access controller from FIGS. 1 and 2 are shown in FIG. 3. The first view 81 shows the output of the first monitor 8 and the second view 91 shows the output of the second monitor 9.

As can be seen, the first view 81 contains a first window 82 in which the finding entered via the keyboard 6 is displayed to a viewer with the corresponding links "(1)", "(2)" to the underlying measurement results. Furthermore, a first button 83 is provided in order to automatically add a link to an underlying measurement result at the immediately-active finding. Furthermore, a list 84 of the links contained in the active finding can be displayed on the first monitor 8.

The second view 91 of the second monitor 9 exhibits a design similar to the first view 81. In a second window 92 of the second view 91, various measurement results $3k1, 3k2, \ldots, 3kl, \ldots, 3km$ are displayed to a patient regarding whom the finding immediately shown in the first display 91 is generated. Furthermore, a second button 93 that enables an automatic addition at an immediately active finding of a link to a measurement result selected in the second view 91 is also provided in the second view 91.

As shown in FIG. 3, an interaction exists between the two views 81, 91 since both monitors 8, 9 are controlled by the access controller 1. This interaction is symbolized by the arrow 1' in FIG. 3.

An actuation of the first button 83 in the first view 81 leads to the access controller 1 automatically establishing which measurement result $3k1, 3k2, \ldots, 3kl, \ldots, 3km$ in the second window 92 of the second view 91 is currently selected. The access controller 1 automatically determines the respective individual identification and stores this in the list of the links 84 at the finding stored in the first file 2. A written reference to the link "(1)", "(2)" . . . is additionally, automatically added to the finding. In this example, the query of a respective unambiguous identification of a referenced measurement result via the inventive access controller 1 thus ensues via the first button 83.

Alternatively or additionally, by actuation of the second button 93 shown in the second view 91, it is possible to store in the immediately active finding the unambiguous individual identification of an immediately selected measurement result by means of the inventive access controller 1, and thus to add the list of the links 84 of the finding.

Furthermore, it is advantageous to allow a link to a measurement result forming the basis of a finding can also be manually entered via the keyboard 6 connected with the access controller 1 and be stored at the respective finding in the first file 2.

Instead of the use of two monitors 8 and 9 as described in the preceding, it is also possible to use only one monitor. In this case, an actuation of the first button 83 in the first view 81 causes a switch from the first view 81 to the second view 91 in order to allow the selection of a measurement result for generation of a link. In this case, an actuation of the second button 93 in the second view 91 preferably causes a change to the first view 81 and to a storage in the immediately active finding of the link to the selected measurement result.

Alternatively, the views 81 and 91 can be simultaneously displayed on one monitor.

In the example shown in FIG. 3, the transfer of the identification between the first file 2 stored on the first server 2 and the second file 3 stored on the second server ensues via a TCP/IP network connection in the form of the XML format. Alternatively, the A7 format or a different network connection can be used.

In a preferred exemplary embodiment, given a selection of an existing link of a finding displayed in the first view 81, the associated measurement result is automatically read out from the second file 3 and is displayed on a monitor 8 or, respectively, 9. Alternatively, it is advantageous when all measurement results cited in an immediately opened finding are automatically loaded and displayed upon the opening of the finding. The time for the study of the finding thus can be further shortened.

In the following, two actual examples of findings are explained with reference to FIGS. 4A and 4B.

The measurement results shown in FIG. 4A concern a patient who has suffered a seizure after multiple months of a sinus infection (paranasal sinusitis).

The associated finding proceeds as follows:

The image "link to $3kl'$" shows a subdural accumulation that exhibits a bright opacity typical of pus. Since blood also causes a bright opacity, it could alternatively be a subdural hematoma as a result of a trauma.

Figure 4B:
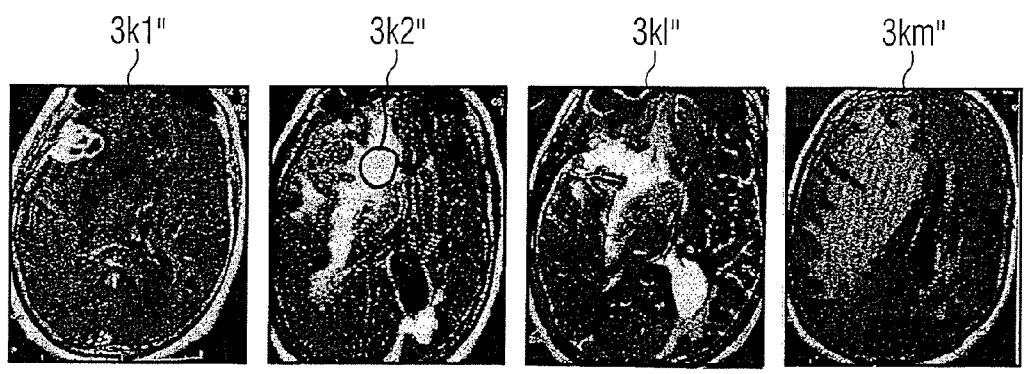
FIG. 4B is a second example of measurement results stored in the second file.

The measurement results shown in FIG. 4B concern a patient who was admitted with headaches and left-side symptoms. In this example, a corresponding finding to be stored in the first file 2 proceeds as follows:

Meningioma (meningeal sarcoma) is a vasogenic edema that can occur in connection with meningiomas (link to $3k2"$; pointer 10). This is particularly clear from the image (link to $3kl"$)

As can be seen, a link to two images (measurement results) is sufficient for the preceding finding. This is in particular noteworthy as up to 400 images of the patient are typically acquired for the diagnosis.

Furthermore, a pointer 10 to a point in the image (measurement result) $3k2"$ is contained in the preceding finding.

From this it is clear that the inventive access controller enables the access in a particularly simple and reliable manner to measurement results $3k1"$, $3kl"$ stored in a second file 3 and forming the basis of a finding $2k$ stored in a first file 2.

A preferred embodiment of the inventive method for controlling the access to medical data is shown in FIG. 5. A finding regarding a patient is recorded in a first step S1 and stored in a first file.

The selection of measurement results of the patient that are stored in a second file and form the basis of the finding ensues subsequently or simultaneously in step S2. The second file is thereby independent of the first file.

In step S3 it is determined whether the design or the structure of the second file allows a direct referencing of the measurement results.

If this is not the case, in the following step S4 a copy of a referenced measurement result stored in the second file is generated, and in step S5 said copy is stored in a third file independent of the first file and second file.

In the following step S6, a designation and/or a storage location of the copy of the at least one measurement result forming the basis of the respective finding is automatically added as a link at the finding stored in the first file.

However, if it is established in step 3 that the second file allows a direct referencing of the measurement results, in step S7 a link to the measurement results forming the basis of the finding is automatically added at the finding stored in the first file.

In step S8 it is subsequently checked whether, in addition to the measurement result, a pointer to specific regions with a measurement result was also selected.

If this is not the case, the method terminates.

Otherwise, in step S9 a pointer to specific individual results in at least one measurement result forming the basis of the respective finding is automatically added in the respective finding stored in the first file before the method terminates.

A finding generated by means of the inventive method allows an automatic identification of measurement results stored in the second or, respectively, third file and forming the basis of the finding using the link stored at the respective finding in the first file.

The finding thus can be checked for accuracy particularly quickly and with high reliability by a doctor performing further treatment.

Although modifications and changes may be suggested by those skilled in the art, it is the intention of the inventors to embody within the patent warranted hereon all changes and modifications as reasonably and properly come within the scope of their contribution to the art.

We claim as our invention:

1. An electronic access controller for accessing medical information, comprising:

at least one server at which a first data file and a second data file are stored with said second data file being stored separately from said first data file, said first data file containing a plurality of findings generated by medical personnel describing a medical state of a patient, and said second file containing images, each comprised of image points, acquired from the patient with a medical imaging apparatus, at least one subset of said images stored in said second file forming a basis for at least one subset of the findings stored in said first file;

said second file being organized to comprise, for each of said images stored therein, an unambiguous identification thereof;

a computerized access controller unit configured to establish a communication path to said at least one server to access said first data file and said second data file;

after establishment of said communication path, said access controller unit being configured to detect one of said subsets of said images and to generate a link only to said one of said subsets of images by specifying identification and by adding a pointer to said link that points to at least one image point in at least one of said images that forms said basis for said at least one subset of findings, and to store said link containing said pointer in said first data file in association with the subset of findings in the first data file for which said one subset of images in the second data file forms the basis;

an electronic information retrieval input unit connected to said computerized access controller unit allowing a user to make an entry that selects one of said subsets of findings stored in said first data file, and said computerized access controller unit being configured to retrieve said one of said subsets of findings from said first data file and, using said link with said pointer therein to also retrieve only said one subset of images from said second data file that form the basis of said one subset of findings in said first data file; and a display connected to said computerized access controller unit at which said computerized access controller unit causes the retrieved one subset of findings and the retrieved one subset of images to be displayed as a displayed image with the pointer pointing, in said displayed image, to said at least one image point.

2. An access controller as claimed in claim 1 wherein said computerizes access controller unit is configured to produce said link as at least one of a designation or a storage location of each of said images in said subset that forms the basis of said at least one subset of findings.

3. An access controller as claimed in claim 2 wherein said computerized access controller unit is configured to allow addition of said link at a finding stored in said first file, and to automatically generate a copy of the image associated with said link in a third file that is independent of said first file and said second file.

4. An access controller as claimed in claim 1 comprising a finding input device and an image selection device connected to said computerized access controller unit, said finding input device allowing recording of findings regarding respective patients and said image selection device allowing selection of images stored in said second file, and wherein said computerized access controller unit is configured to automatically generate, based on a selected measurement result, a link to the selected measurement results and to store said link at the finding in the first file.

5. An access controller as claimed in claim 1 wherein said at least one server comprises a first memory containing said first file and a second memory, different from said first memory, containing said second file.

6. An electronic access controller as claimed in claim 1 wherein said sever stores medical images of the patient as said examination results in said second data file, and wherein said access controller unit is configured to retrieve and display one of said images as said one subset of examination results from said second data file that forms the basis of said one subset of findings in said first data file and, in the displayed image, to designate with said pointer a region within the displayed image that forms the basis of said one subset of findings in said first data file.

7. A method for accessing medical information, comprising the steps of:

storing a first data file and a second data file at at least one server with said second data file being stored independently of said first data file, and in said first data file, storing a plurality of findings generated by medical personnel describing a medical state of a patient, and in said second file, storing images, each comprised of image points, acquired from the patient with a medical imaging apparatus, at least one subset of said images stored in said second file forming a basis for at least one subset of the findings stored in said first file;

organizing said second file to comprise, for each of said images stored therein, an unambiguous identification thereof;

through a computerized access controller unit, establishing a communication path to said at least one server to access said first data file and said second data file;

after establishment of said communication path, through said access controller unit, detecting one of said subsets of said images and generating a link only to said one of said subsets of images by specifying identification and by adding a pointer to said link that points to at least one image point in at least one of said images that forms said basis for said at least one subset of findings, and storing said link containing said pointer in said first data file associated with the subset of findings in the first data file for which said one subset of images in the second data file form the basis; and through an electronic information retrieval input unit connected to said computerized access controller unit, making an entry that selects one of said subsets of findings stored in said first data file, and through said access controller unit, retrieving said one of said subsets of findings from said first data file and, using said link with said pointer, also retrieving only said one subset of images from said second data file that form the basis of said one subset of findings in said first data file; and at a display connected to said computerized access controller unit, displaying the retrieved one subset of findings and the retrieved one subset of images as a displayed image with the pointer pointing, in said displayed image, to said at least one image point.

8. A method as claimed in claim 7 comprising producing said link as at least one of a designation or a storage location of each of said images in said subset that form the basis of said at least one subset of findings.

9. A method as claimed in claim 8 comprising adding said link at a finding stored in said first file, and automatically generating a copy of the image associated with said link in a third file that is independent of said first file and said second file.

10. A method as claimed in claim 7 comprising, via a finding input device, allowing recording of findings regarding respective patients and, via an image selection device, allowing selection of images stored in said second file, and comprising automatically generating, based on a selected image, a link to the selected images and storing said link at the finding in the first file.

11. A method as claimed in claim 7 comprising organizing said second file as a data bank file, with respective entries for said images.

12. A method as claimed in claim 7 comprising organizing said second file as a plurality of folder files, with images being subordinate files in the respective folder file.

13. A method as claimed in claim 7 comprising storing said first file in a first memory and storing said second file in a second memory, different from said first memory.

* * * * *